(12) United States Patent
Ishii et al.

(10) Patent No.: US 10,188,415 B2
(45) Date of Patent: Jan. 29, 2019

(54) FORCEPS AND FORCEPS UNIT

(75) Inventors: Masanori Ishii, Kofu (JP); Minoru Hirata, Ichikawa (JP)

(73) Assignees: MASANORI ISHII, Kofu-Shi, Yamanashi (JP); HIRATA PRECISIONS CO., LTD., Ichikawa-Shi, Chiba (JP)

( * ) Notice: Subject to any disclaimer, the term of this patent is extended or adjusted under 35 U.S.C. 154(b) by 934 days.

(21) Appl. No.: 14/122,177

(22) PCT Filed: Aug. 12, 2011

(86) PCT No.: PCT/JP2011/068478
§ 371 (c)(1),
(2), (4) Date: Nov. 25, 2013

(87) PCT Pub. No.: WO2012/160715
PCT Pub. Date: Nov. 29, 2012

(65) Prior Publication Data
US 2014/0107690 A1  Apr. 17, 2014

(30) Foreign Application Priority Data

May 26, 2011 (JP) .................................. 2011-118534

(51) Int. Cl.
*A61B 17/28* (2006.01)
*A61B 17/29* (2006.01)
(Continued)

(52) U.S. Cl.
CPC ............. *A61B 17/28* (2013.01); *A61B 17/29* (2013.01); *A61B 17/3415* (2013.01);
(Continued)

(58) Field of Classification Search
CPC ................ A61B 17/29; A61B 17/3415; A61B 2017/2901; A61B 2017/0046;
(Continued)

(56) References Cited

U.S. PATENT DOCUMENTS 4,919,152 A * 4/1990 Ger ..................... A61B 17/29
128/898
6,077,290 A * 6/2000 Marini .................. A61B 17/29
600/564
(Continued)

FOREIGN PATENT DOCUMENTS

JP  7-265321 A  10/1995
JP  7-299075 A  11/1995
(Continued)

OTHER PUBLICATIONS

International Search Report from the Japanese Patent Office in counterpart International Application No. PCT/JP2011/068478, dated Nov. 15, 2011, 1 page.
(Continued)

*Primary Examiner* — Diane Yabut
*Assistant Examiner* — Erich Herbermann
(74) *Attorney, Agent, or Firm* — Stephen J. Weyer, Esq.; Stites & Harbison, PLLC

(57) ABSTRACT

Forceps include a tubular shaft, an inserted member, a gripping portion, a handle, and a fixing portion. The inserted member is a rod-like member that is inserted inside the tubular shaft and is movable in an axial direction inside the tubular shaft. The gripping portion is provided at a distal end of the inserted member and is coupled to a distal end of the tubular shaft. The handle is coupled to a terminal end of the inserted member. The fixing portion detachably fixes the handle to the tubular shaft in a state where the handle is coupled to the inserted member. The distal end of the tubular shaft has a larger diameter than the diameter of a main body of the tubular shaft. A joint portion, having a smaller diameter than the diameter of the main body of the tubular shaft, is formed at the terminal end of the inserted member. The handle is provided with a joint receptacle that houses the joint portion and is advanced and retracted by manipulation of the handle.

11 Claims, 17 Drawing Sheets

(51) Int. Cl.
  *A61B 17/00* (2006.01)
  *A61B 17/34* (2006.01)
(52) U.S. Cl.
  CPC ........ *A61B 2017/0046* (2013.01); *A61B 2017/00477* (2013.01); *A61B 2017/2901* (2013.01)
(58) Field of Classification Search
  CPC ......... A61B 2017/00477; A61B 17/02; A61B 17/34158; A61B 17/28
  USPC ...................................... 279/42, 43; 606/205
  See application file for complete search history.

(56) References Cited

U.S. PATENT DOCUMENTS

| | | | | |
|---|---|---|---|---|
| 8,956,341 | B2* | 2/2015 | Chen | A61B 17/29 600/204 |
| 2005/0125027 | A1* | 6/2005 | Knodel | A61B 17/29 606/205 |
| 2008/0294192 | A1* | 11/2008 | Stefan | A61B 17/1608 606/205 |
| 2009/0187073 | A1* | 7/2009 | Karasawa | A61B 1/041 600/114 |
| 2010/0298774 | A1 | 11/2010 | Igov | |

FOREIGN PATENT DOCUMENTS

| | | |
|---|---|---|
| JP | 2005-013296 A | 1/2005 |
| JP | 2006-341111 A | 12/2006 |
| JP | 2008-534045 A | 8/2008 |

OTHER PUBLICATIONS

Notification of Transmittal of Translation of the International Preliminary Report on Patentability (IPRP) from the International Bureau in counterpart International Application No. PCT/JP2011/068478, dated Nov. 28, 2013, pp. 1-5.

* cited by examiner

FORCEPS AND FORCEPS UNIT

TECHNICAL FIELD

The present invention relates to forceps or a forceps unit used, for example, in performing laparoscopic surgery.

BACKGROUND ART

As conventional forceps used in laparoscopic surgery, there is known those with which a gripping structure, capable of opening and closing and provided at a distal end portion of a tubular shaft 1 of small diameter, is remotely manipulated to open and close at an opposite end that is a proximal portion (see, for example, Patent Literature 1). In the present description, this gripping structure at the forceps distal end portion shall be referred to as the "gripping portion" and in particular, a gripping portion having an alligator-mouth-like shape shall be referred to as an "alligator portion." As shown in FIG. 17, with the alligator portion 2, a pair of gripping members A and B are connected to be mutually rotatable around a rotation axis of a fulcrum portion 3. More specifically, each of the gripping members A and B has an action point portion 4 applying a force for gripping on an object to be gripped and a power point portion 5 to which the force for gripping is applied from the manipulating side. Also, at the action point portions 4, grooves for gripping the object favorably are provided as necessary on object-facing surfaces 4a and 4b that directly contact the object. With such an arrangement, when a force for opening/closing is applied from the opposite end, which is the proximal portion, to the power point portions 5 using a wire (inserted member) 7, etc., coupled to a handle 6, the gripping members A and B, for example, rotate around the rotation axis of the fulcrum portion 3 and close to enable gripping of the object.

The above-described forceps are used in various processes where an object deep inside a narrow gap needs to be gripped. For example, such forceps are useful in laparoscopic surgery (see, for example, Patent Literature 2). In a laparoscopic surgery described in Patent Literature 2, a plurality of communicating tubes called trocars are penetrated through an abdominal wall and inserted into an abdominal cavity, the interior of the abdominal cavity is observed as a monitor image using a compact camera (endoscope) inserted from one of the trocars, and while viewing the monitor image, various surgical procedures are performed inside the abdominal cavity using instruments, such as forceps, scissors, scalpel, needle holder, etc., inserted through the other trocars.

As forceps used in such laparoscopic surgery, general forceps, with the diameter of the tubular shaft being approximately 5 mm, and small-diameter forceps, with the diameter of the tubular shaft being approximately 2 mm, are known. Ordinary forceps are inserted in a trocar, for example, with a diameter of approximately 5 mm. Small-diameter forceps are inserted in a small-diameter port (trade name: Mini-Port) with a diameter of approximately 2 mm (more specifically, 2.4 mm).

CITATION LIST

Patent Literature

Patent Literature 1: Japanese Patent Application Laid-Open No. H07-299075

Patent Literature 2: Japanese Patent Application Laid-Open No. H07-265321

SUMMARY OF INVENTION

Technical Problem

In surgery, it is desirable for a surgical wound to be made as small as possible. It is thus preferable to adopt small-diameter forceps that can be passed through a small-diameter port. To pass the small-diameter forceps through the small-diameter port, the diameter of the entire small-diameter forceps, including the gripping portion attached to the distal end portion thereof, must be of a size that is in accordance with the small-diameter port. However, in some cases where the gripping portion and the distal end portion of the tubular shaft are made small, the strength thereof is insufficient. Also, the strength of pinching an affected portion is weak and therefore a restriction may be placed on the tissue that can be gripped.

Therefore in the present field, forceps and a forceps unit capable of making a surgical wound small and yet capable of gripping a tissue appropriately inside an abdominal cavity are being desired.

Solution to Problem

Forceps according to one aspect of the present invention are forceps for gripping tissue inside an abdominal cavity. The forceps include a tubular shaft, an inserted member, a gripping portion, a handle, and a fixing portion. The inserted member is a rod-like member that is inserted inside the tubular shaft and is movable in an axial direction inside the tubular shaft. The gripping portion is provided at a distal end of the inserted member and is coupled to a distal end of the tubular shaft. The handle is coupled to a terminal end of the inserted member. The fixing portion detachably fixes the handle to the tubular shaft in a state where the handle is coupled to the inserted member. The distal end of the tubular shaft has a larger diameter than the diameter of a main body of the tubular shaft. A joint portion, having a smaller diameter than the diameter of the main body of the tubular shaft, is formed at the terminal end of the inserted member. The handle is provided with a joint receptacle that houses the joint portion and is advanced and retracted by manipulation of the handle.

With these forceps, the diameter of the distal end of the tubular shaft is larger than the diameter of the main body and therefore strength can be maintained in comparison to a case where the gripping portion is attached to a tubular shaft having a distal end with the same diameter as the main body. The size of the mounted gripping portion can thus be made large in accordance with the size of the distal end of the tubular shaft. Gripping of various tissues can thus be accommodated. Also, by the handle being detachable from the tubular shaft and the joint portion of the tubular shaft being smaller in diameter than the diameter of the main body of the tubular shaft, instead of inserting the forceps into the abdominal cavity starting from the distal end of the tubular shaft, the handle can be detached, the forceps (without the handle) can be inserted into the abdominal cavity starting from a terminal end of the tubular shaft, and the terminal end of the tubular shaft can be drawn outside the abdominal cavity to attach the handle. That is, the size of a surgical wound for using the forceps can be made approximately the same in size as a hole enabling insertion of the terminal end and the main body of the tubular shaft. The size of the surgical wound can thus be made small regardless of the size of the distal end of the forceps or the size of the gripping portion.

Also, the handle and the inserted member are coupled by the joint portion of the inserted member being housed in the joint receptacle of the handle member. The handle and the tubular shaft are fixed by the fixing portion. By having such an arrangement, a detachable coupling structure can be realized without enlarging the sizes of the diameters of the inserted member and the tubular shaft that influence the size of the surgical wound.

In an embodiment, the tubular shaft may be formed so that the size of its diameter changes gradually. By arranging thus, the strength of the forceps can be further increased.

In the embodiment, the fixing portion may include a chuck member and a fixing ring. The chuck member may have an insertion hole formed therein and may have a projecting step portion, for locking the terminal end of the tubular shaft in the axial direction, provided along an inner circumference of the insertion hole. The fixing portion may have an insertion hole formed therein and be coupled to a coupling portion provided on the handle. The chuck member may be fixed by the fixing ring to the handle in a state where the terminal end of the tubular shaft, with the inserted member inserted therein, is inserted in the chuck member, the joint receptacle of the handle and the joint portion of the inserted member are coupled, the chuck member is sandwiched between the fixing ring and the handle, and the terminal end of the tubular shaft is abutted against the projecting step portion of the chuck member. By arranging thus, a detachable coupling structure can be realized.

Also, a forceps unit according to another aspect of the present invention is a forceps unit including forceps for gripping a tissue. The forceps unit includes a trocar, the forceps, and a small-diameter port. The trocar serves as a portion for insertion into an abdominal cavity. The forceps include a tubular shaft, an inserted member, a gripping portion, a handle, and a fixing portion. The inserted member is a rod-like member that is inserted inside the tubular shaft and is movable in an axial direction inside the tubular shaft. The gripping portion is provided at a distal end of the inserted member and is coupled to a distal end of the tubular shaft. The small-diameter port is a port of small diameter that serves as a portion for drawing out the tubular shaft from inside the abdominal cavity. The distal end of the tubular shaft has a larger diameter than the diameter of a main body of the tubular shaft and the diameter of an insertion hole of the small-diameter port. The main body and a terminal end of the tubular shaft have diameters smaller than the diameter of the insertion hole of the small-diameter port. A joint portion, having a smaller diameter than the diameters of the main body and the terminal end of the tubular shaft, is formed at the terminal end of the inserted member. The handle is provided with a joint receptacle that houses the joint portion and is advanced and retracted by manipulation of the handle.

With these forceps, the diameter of the distal end of the tubular shaft is larger than the diameter of the main body and therefore strength can be maintained in comparison to a case where the gripping portion is attached to a tubular shaft having a distal end with the same diameter as the main body. The size of the mounted gripping portion can thus be made large in accordance with the size of the distal end of the tubular shaft. Gripping of various tissues can thus be accommodated. Also, by the handle being detachable from the tubular shaft and the joint portion of the tubular shaft being smaller in diameter than the diameter of the main body of the tubular shaft, instead of inserting the forceps into the abdominal cavity starting from the distal end of the tubular shaft, the handle can be detached, the forceps (without the handle) can be inserted into the abdominal cavity starting from the terminal end of the tubular shaft, and the terminal end of the tubular shaft can be drawn outside the abdominal cavity via the small-diameter port to attach the handle. That is, the size of a surgical wound for using the forceps can be made approximately the same in size as a hole enabling insertion of the terminal end and the main body of the tubular shaft. The size of the surgical wound can thus be made small regardless of the size of the distal end of the forceps or the size of the gripping portion.

The embodiment may further include a tubular shaft member that is connectable to the terminal end of the inserted member and has a smaller diameter than the diameter of the insertion hole of the small-diameter port. By the shaft guide member being included, it is possible, before inserting the forceps, with the handle removed, into the trocar, to insert one end portion of the shaft guide member into the small-diameter port and draw out the one end portion of the shaft guide member via the trocar and connect it to the terminal end of the inserted member without the other end portion of the shaft guide member being inserted into the abdominal cavity. By then extracting the other end portion of the shaft guide member from the small-diameter port, the terminal end of the tubular shaft can be drawn out easily from the abdominal cavity.

Advantageous Effects of Invention

By the present invention, forceps and a forceps unit capable of making a surgical wound small and yet capable of gripping a tissue appropriately inside an abdominal cavity can be provided.

DESCRIPTION OF EMBODIMENTS

Figure 1:
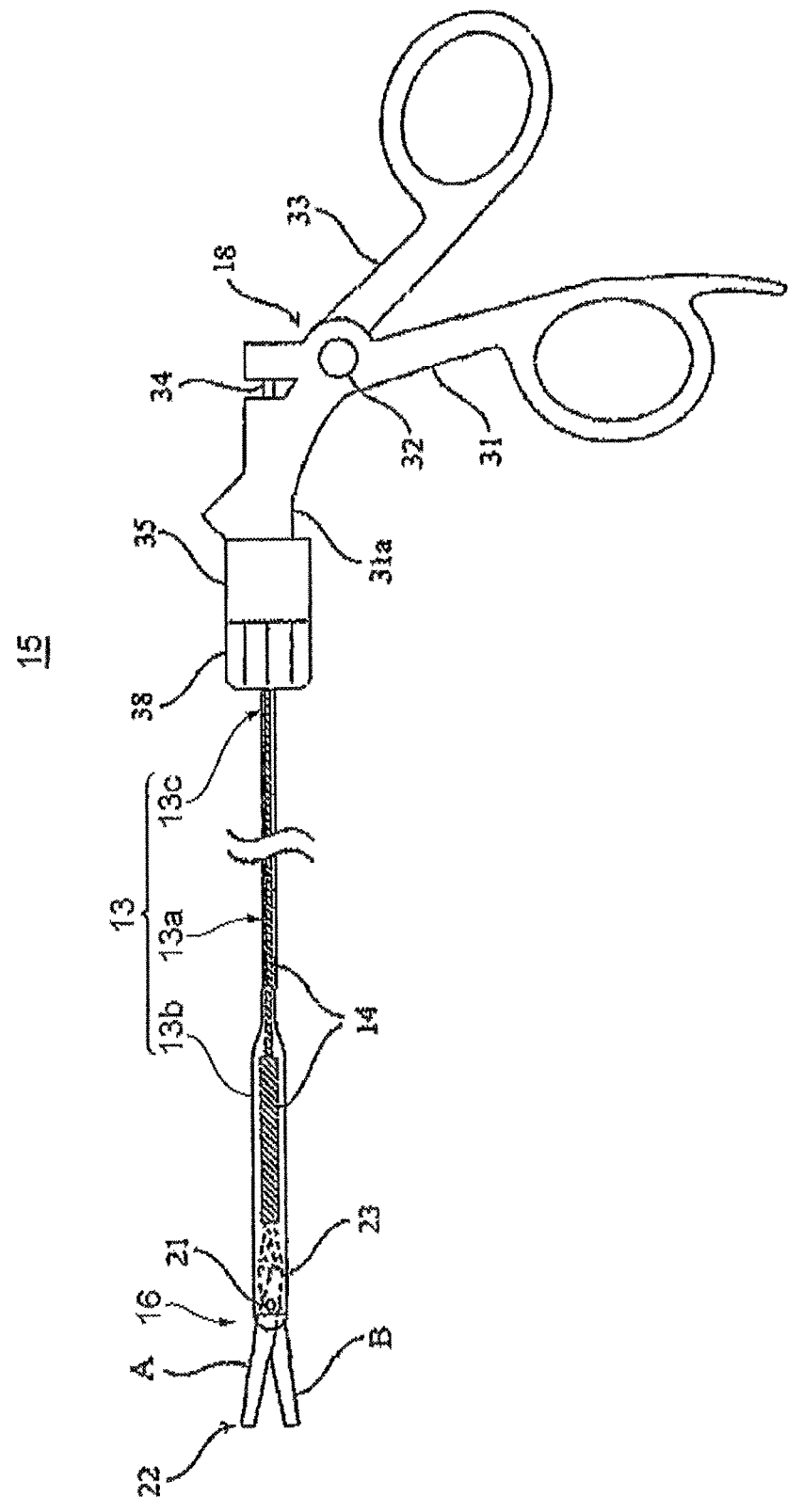
FIG. 1 is a side view of forceps according to an embodiment.
Figure 2:
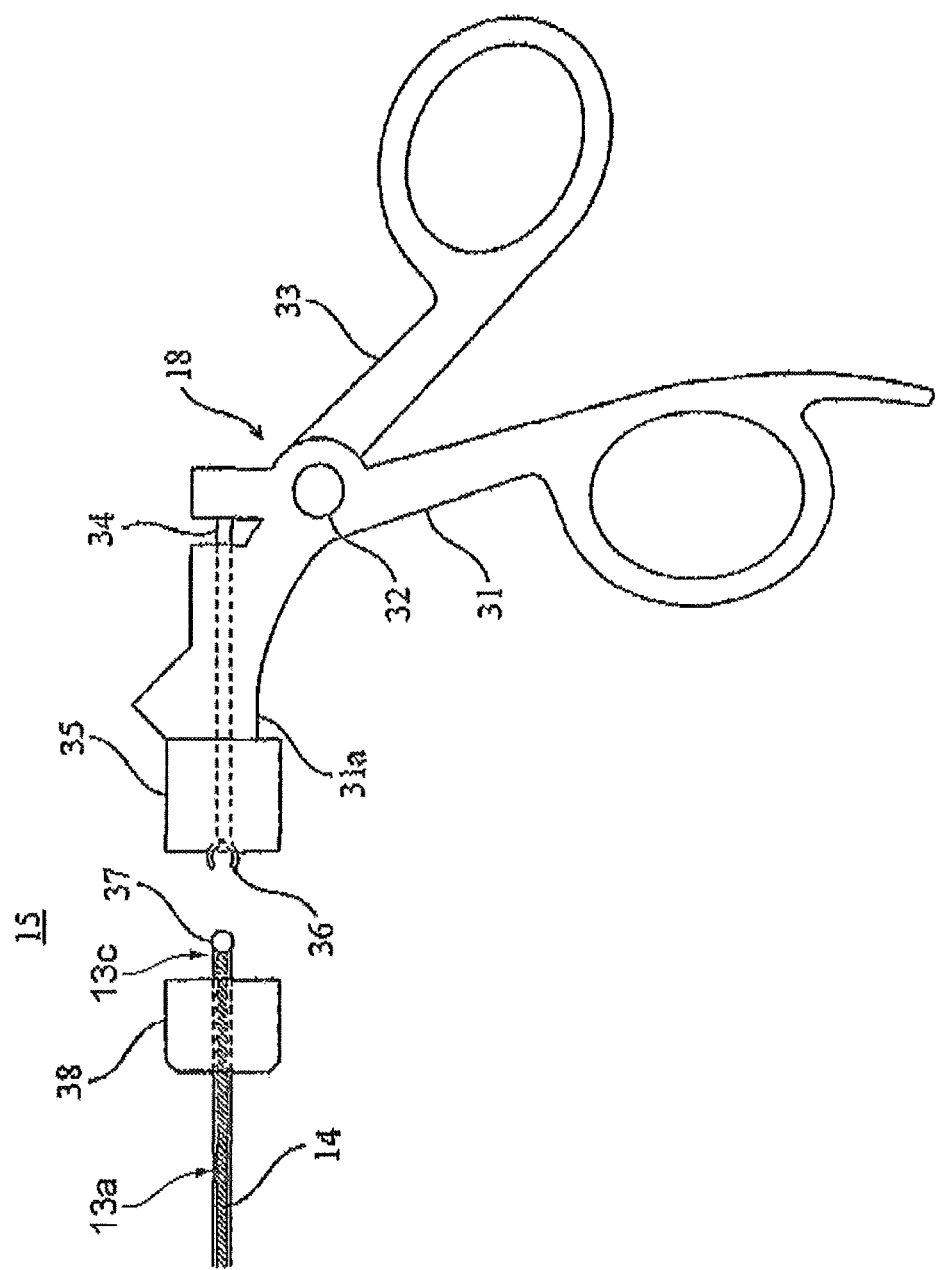
FIG. 2 is an enlarged view of an example of a mechanism for coupling a tubular shaft and a handle of the forceps according to the embodiment.
Figure 4:
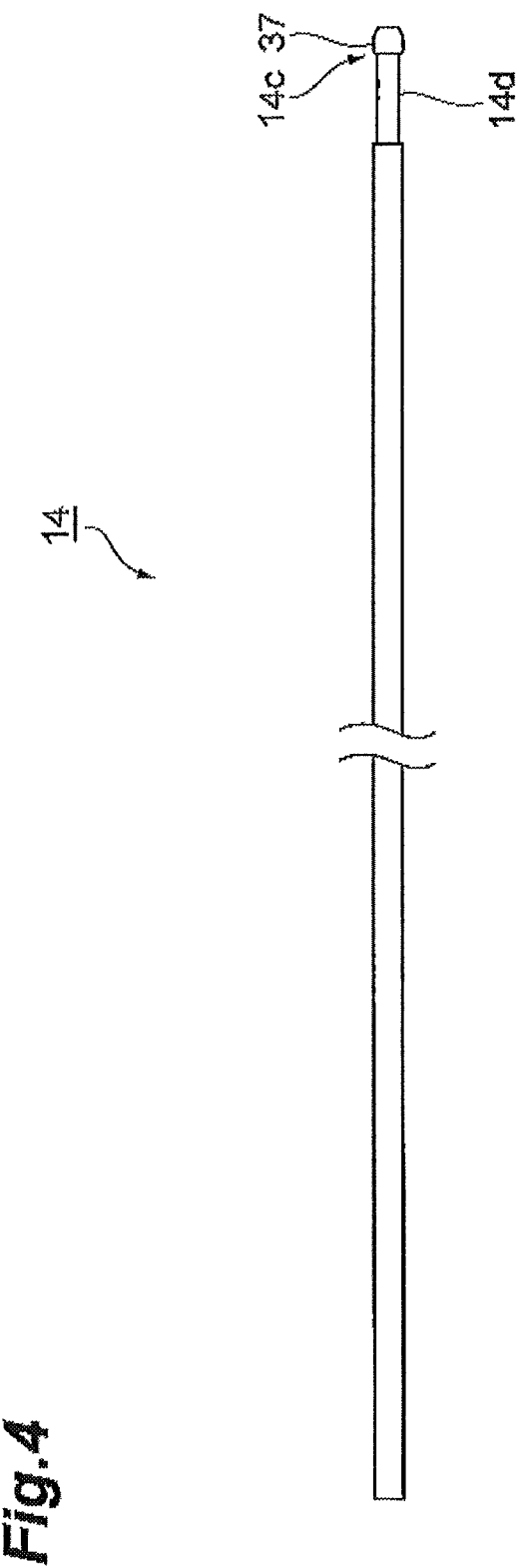
FIG. 4 is a side view of an inserted member of the forceps according to the embodiment.
Figure 5:
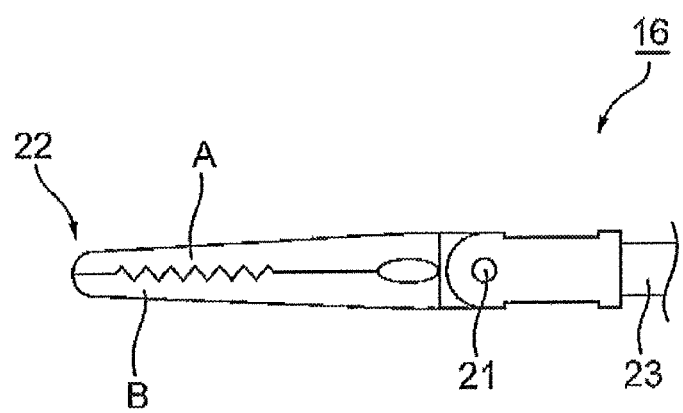
FIG. 5 is a side view of a gripping portion of the forceps according to the embodiment.

Forceps and a forceps unit for laparoscopic surgery according to an embodiment shall now be described in detail based on the drawings. FIG. 1 is a side view of the forceps, FIG. 2 is an enlarged view of an example of a mechanism for coupling a tubular shaft and a handle, FIG. 3 is a side view of the tubular shaft, FIG. 4 is a side view of an inserted member, and FIG. 5 is a side view of a gripping portion.

As shown in FIG. 1, the small-diameter forceps (forceps) 15 according to the embodiment includes the tubular shaft 13, the inserted member 14, the gripping portion (alligator portion) 16, the fixing ring (fixing portion) 38, and the handle 18.

Figure 3:
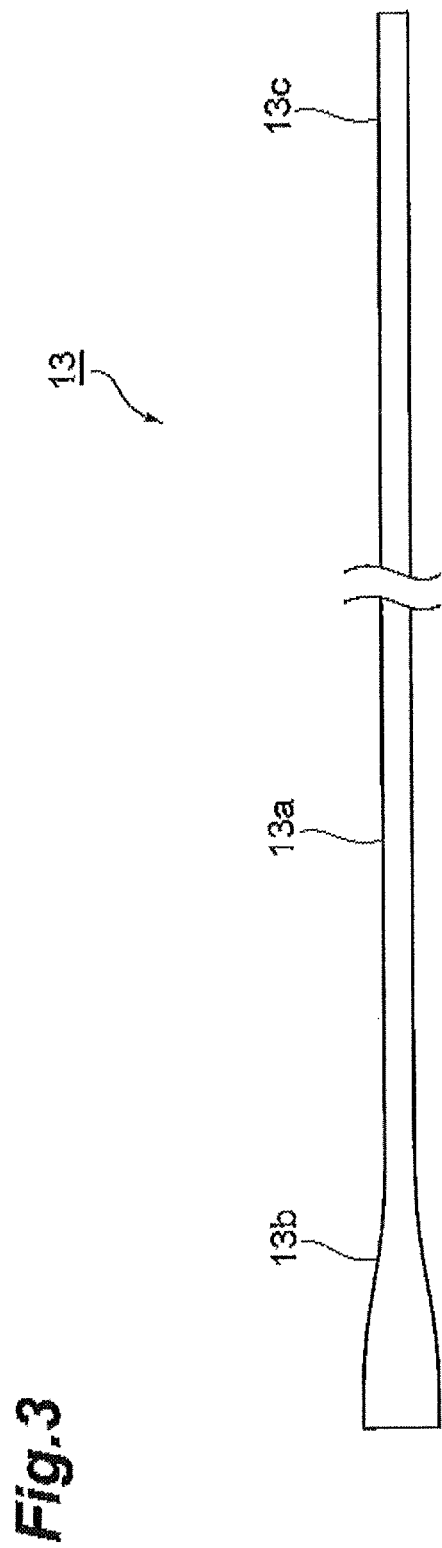
FIG. 3 is a side view of the tubular shaft of the forceps according to the embodiment.

As shown in FIGS. 1 and 3, the tubular shaft 13 is a member having a penetrating hole formed in an axial direction. The inserted member 14 and a portion of the gripping portion 16 are housed in the interior of the tubular shaft 13. The tubular shaft 13 is formed, for example, of a metal. Also, the tubular shaft 13 is made smaller in diameter than the inner diameter of a trocar 12 to be described below. For example, when the inner diameter of the trocar 12 is greater than 5 mm, the tubular shaft 13 is made no more than 5 mm in diameter.

With the tubular shaft 13, the diameter of a distal end 13b is expanded in comparison to the diameters of a terminal end 13c and a main body 13a. That is, the distal end 13b of the tubular shaft 13 has a larger diameter than the diameter of the main body 13a of the tubular shaft 13. The tubular shaft 13 is formed so that the size of its diameter changes gradually. For example, the size of the diameter increases gradually from the main body 13a toward the distal end 13b until the diameter of the distal end 13b is attained. In other words, the tubular shaft 13 is squeezed gradually from an intermediate portion as the terminal end 13c is approached from the distal end 13b and is narrowed in tapered form until the diameter of the main body 13a is attained. The strength of the tubular shaft 13 is maintained sufficiently by such a structure.

As shown in FIGS. 1 and 4, the inserted member 14 is a rod-like member that is inserted inside the tubular shaft 13. That is, the inserted member 14 has a diameter that is smaller than the inner diameter of the tubular shaft 13 and is arranged to be movable inside the tubular shaft 13. A joint portion 37 for coupling with the handle 18 is formed at a terminal end 14c of the inserted member 14. The joint portion 37 has a smaller diameter than the diameter of the main body 13a of the tubular shaft 13. The joint portion 37 is formed, for example, by chipping off the outer periphery of the inserted member 14 to form a groove 14d. The joint portion 37 may be processed in accordance with the shape of a joint receptacle to be described later. For example, the joint portion 37 is processed to a ball shape. By being processed to a ball shape, damaging of the interior of an abdominal cavity can be avoided during insertion into the abdominal cavity to be described below. The inserted member 14 moves inside the tubular shaft 13 in the axial direction in accordance with a handle manipulation of the handle 18 to be described below. The inserted member 14 may have a thickness aligned with the size of the inner diameter of the tubular shaft 13. The inserted member 14 may be formed as an integral component regardless of the thicknesses of its respective portions. The inserted member 14 is formed, for example, of a metal.

As shown in FIGS. 1 and 2, the handle 18 is coupled to the terminal end 13c of the tubular shaft 13. The handle 18 includes a fixed member 31, in turn including a cylindrical main body 31a, and a movable member 33, rotatably pivoted via a rotation shaft 32 to a predetermined position of the fixing member 31. A pulling lever 34 is coupled to a position on the opposite side of the rotation shaft 32 from the movable member 33. Also, a coupling portion (fixing portion) 35 is attached to a front portion of the cylindrical main body 31a of the fixed member 31. A joint receptacle 36 is disposed at a front surface of a coupling portion 35. The joint receptacle 36 is arranged to be advanced and retracted by the pulling lever 34. The handle 18 is detachably fixed to the tubular shaft 13 in a state of being coupled to the inserted member 14. The fixing ring 38 is a component that detachably fixes and couples the handle 18 and the tubular shaft 13. The coupling structure of the handle 18, the inserted member 14, and the tubular shaft 13 shall be described later.

The gripping portion 16 is provided at a distal end of the inserted member 14 and is coupled to the distal end 13b of the tubular shaft 13. By this structure, the inserted member 14 is moved by manipulation of the handle 18 and the gripping portion 16 operates in accordance with the movement of the inserted member 14. Also, by the gripping portion 16 being coupled to the distal end 13b of the tubular shaft 13, the strength of the gripping portion 16 is maintained.

As shown in FIGS. 1 and 5, the gripping portion 16 includes gripping members A and B. Each of the gripping members A and B has a distal end portion 22 applying a force for gripping on an object to be gripped and a pulling portion 23 to which the force for gripping is applied by the handle 18. Also, at the distal end portions 22, grooves for gripping the object favorably are provided as necessary on object-facing surfaces 22a and 22b that directly contact the object. With such an arrangement, when the handle 18 is manipulated to apply a force for opening/closing to the pulling portions 23 using the inserted member 14, etc., the distal end portions 22, for example, rotate around a rotation shaft 21 that is a fulcrum and close to enable gripping of the object. The gripping portion 16 may be changed to any of various sizes in accordance with usage. For example, the gripping portion 16 may have a larger cross section than the center 13a and the terminal end 13c of the tubular shaft 13. Also, the gripping portion 16 may be the same in structure as that of the conventional forceps with a diameter of 5 mm. That is, excellent versatility is provided because the gripping portion of the conventional forceps can be adopted. The coupling structure of the gripping portion 16 and the inserted member 14 may further be made the same in structure as that of the conventional forceps with a diameter of 5 mm and the durability of the gripping portion 16 can therefore be made the same as that of the conventional forceps with a diameter of 5 mm. Also, the gripping portion 16 provided at the distal end of the tubular shaft 13 of the small-diameter forceps 15 may be formed integral to the tubular shaft 13. FIG. 1 shows an example where the distal end 13b of the tubular shaft 13 is made thick in itself to arrange the gripping portion 16 integrally.

The coupling structure of the handle 18, the inserted member 14, and the tubular shaft 13 shall now be described in outline.

As shown in FIG. 2, the handle 18 and the inserted member 14 are coupled by the joint portion 37 of the inserted member 14, disposed at the terminal end 13c portion of the tubular shaft 13, being attached to the joint receptacle 36 of the handle 18. The fixing ring 38 is disposed at the outer periphery of an end portion of the tubular shaft 13. The handle 18 and the tubular shaft 13 are coupled by the fixing ring 38 being coupled to the coupling portion 35 at the front portion of the cylindrical main body 31a of the handle 18. As a coupling means of the coupling portion 35 and the fixing ring 38, a suitable means, such as that of a screw type, magnet type, clamp type, etc., may be adopted. The handle 18 is thus attached detachably to the terminal end 13c of the tubular shaft 13.

Figure 6:
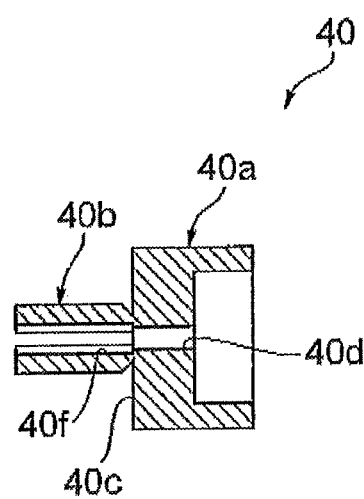
FIG. 6 is a sectional view of a chuck member of the forceps according to the embodiment.
Figure 7:
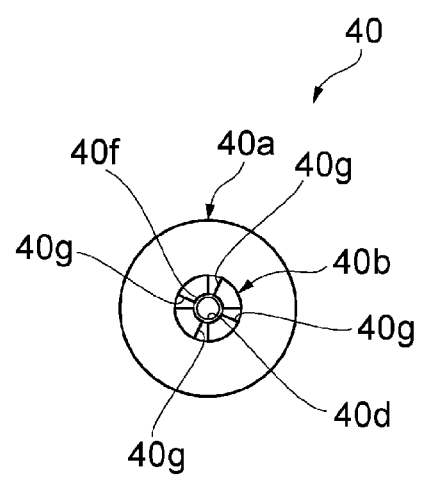
FIG. 7 is a top view of the chuck member of the forceps according to the embodiment.

The coupling structure of the handle 18, the inserted member 14, and the tubular shaft 13 is not restricted to the coupling structure described above. For example, a coupling structure using a chuck member (fixing portion) as described below may be adopted. FIG. 6 is a sectional view of the chuck member, FIG. 7 is a top view of the chuck member, FIG. 8 is a sectional view of the fixing ring 38, and FIG. 9 is an assembly diagram of the forceps.

The chuck member is a member for locking the terminal end of the tubular shaft 13 in the axial direction. As shown in FIGS. 6 and 7, a chuck member 40 has a circular cylindrical main body portion 40a and a tubular guide portion 40b. The circular cylindrical main body portion 40a has a narrow pathway 40d formed in a bottom portion 40c. The narrow pathway 40d is formed to be smaller in size than the diameter of the tubular shaft 13 and yet be greater than the diameter of the inserted member 14. The guide portion 40b is a member that guides the tubular shaft 13 and the inserted member 14. The guide portion 40b is attached to the bottom portion 40c of the main body portion 40a so that its axis passes through the center of the narrow pathway 40d of the main body portion 40a. That is, the interior of the guide portion 40b and the narrow pathway 40d of the main body portion 40a are in communication and form an insertion hole for insertion of the tubular shaft 13 and the inserted member 14. The inner diameter of the guide portion 40b is formed to be greater than the diameter of the narrow pathway 40d and the diameter of the tubular shaft 13. By this arrangement, projecting step portions 40f are formed along the inner periphery of the insertion hole made up of the interior of the guide portion 40b and the narrow pathway 40d. Slits 40g are formed along the axial direction in the guide portion 40b to facilitate attachment and detachment of the chuck member 40.

Figure 8:
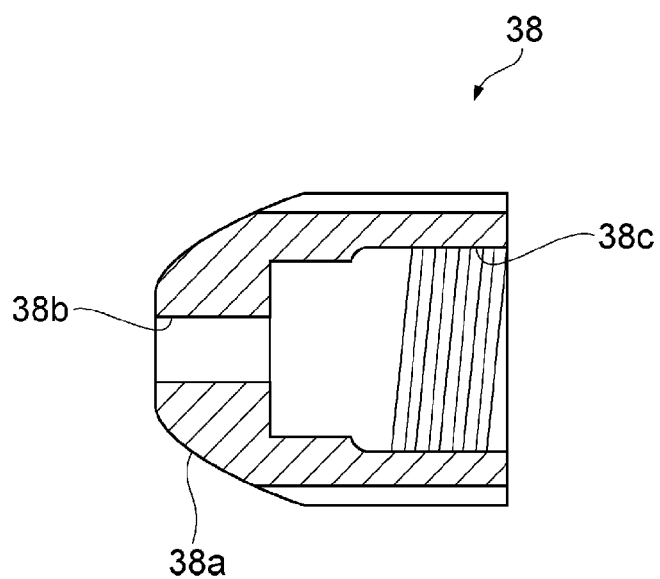
FIG. 8 is a sectional view of a fixing ring of the forceps according to the embodiment.

As shown in FIG. 8, the fixing ring 38 has a circular cylindrical main body portion. An insertion hole 38b of small diameter is formed in a bottom portion 38a. The interior of the main body portion has a size, for example, that enables housing of the main body portion 40a of the chuck member 40. The insertion hole 38b has a size, for example, that enables housing of the guide portion 40b of the chuck member 40. That is, the fixing ring 38 is arranged to be capable of housing the chuck member 40. Also, a female thread portion 38c for coupling with a male thread portion (coupling portion 35) provided on the handle 18 is formed on the inner surface of the main body portion.

Figure 9:
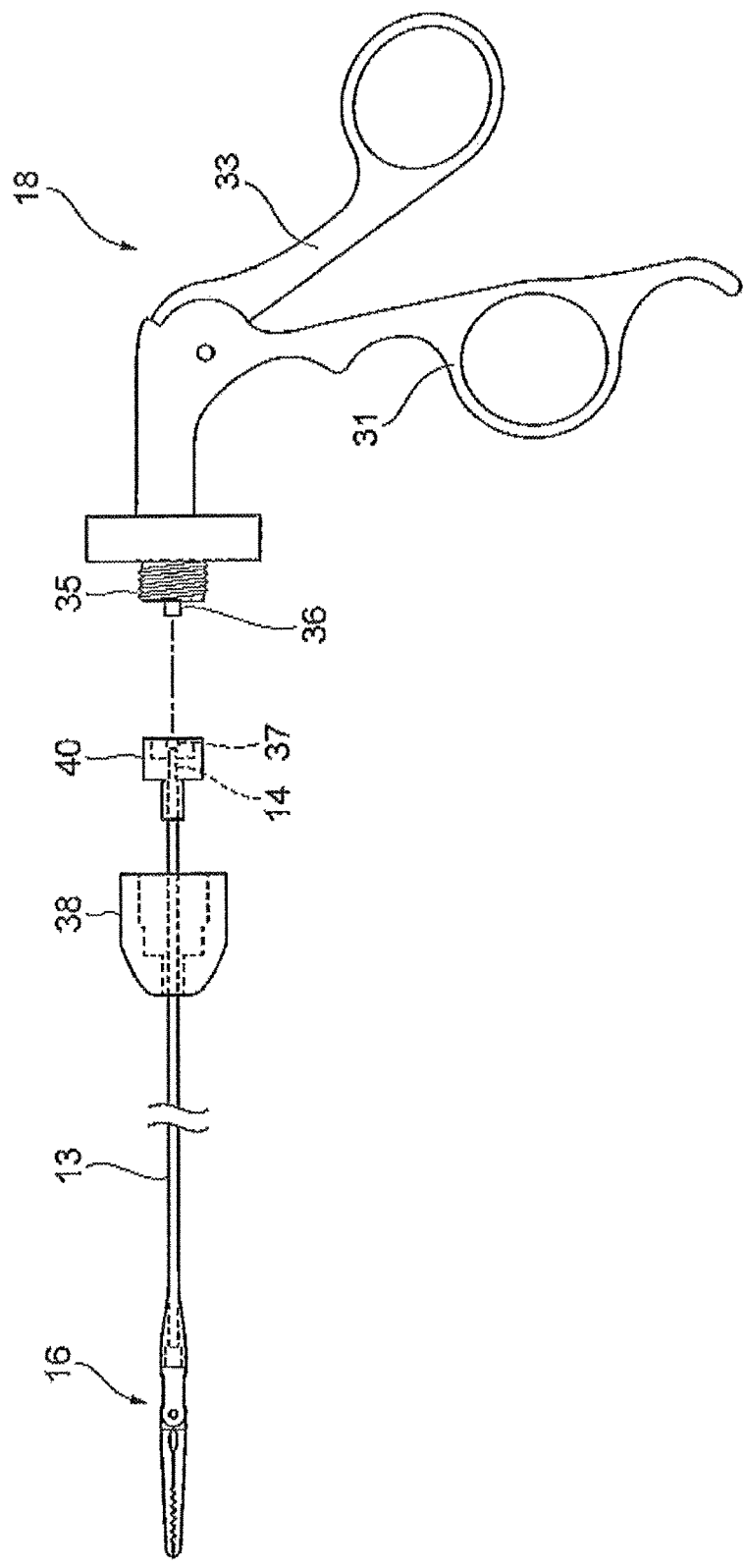
FIG. 9 is an assembly diagram of the forceps according to the embodiment.

As shown in FIG. 9, the terminal end of the tubular shaft 13 with the inserted member 14 inserted therein is inserted through the insertion hole 38b of the fixing ring 38 and the guide portion 40b of the chuck member 40. The joint receptacle 36 of the handle 18 and the joint portion 37 of the inserted member 14 are coupled. Further, the chuck member 40 is sandwiched between the fixing ring 38 and the handle 18 so that the terminal end of the tubular shaft 13 is put in a state of being abutted against the projecting step portions 40f of the chuck member 40. In this state, the fixing ring 38 houses the chuck member 40 and is coupled to the coupling portion 35 of the handle 18. The chuck member 40 is thereby fixed to the handle 18. That is, the tubular shaft 13 fitted with the chuck member 40 is fixed to the handle 18. A detachable connection mechanism can thus be realized without making the end portion of the inserted member 14 large.

A forceps unit for laparoscopic surgery shall now be described. A forceps unit 11 is arranged from at least the following members.

1) The trocar 12 of a predetermined size that is to be a portion inserted inside an abdominal cavity.
2) The small-diameter forceps 15 including the tubular shaft 13, with a smaller diameter than the inner diameter of the trocar 12 that is to be the portion inserted inside the abdominal cavity, the inserted member 14 inserted inside the tubular shaft 13, the gripping portion 16 provided at the distal end of the tubular shaft 13 and substantially equal to the inner diameter of the trocar 12, and the handle 18 detachably attached to the terminal end portion of the tubular shaft 13, and
3) a small-diameter port 17 of small diameter that is to be a portion for drawing out the tubular shaft 13 from inside the abdominal cavity.

As shown in FIG. 10 to FIG. 14, the trocar 12 of the predetermined size that is to be the portion inserted inside the abdominal cavity and is inserted into an abdominal region has an inner diameter of approximately 5 mm and thus has an inner diameter size enabling the insertion of the distal end 13b of the tubular shaft 13 of the small-diameter forceps 15. Similarly as shown in FIG. 10 to FIG. 14, the small-diameter port 17 of small diameter that is inserted in the abdominal region at a different position from the trocar 12 has an inner diameter of approximately 2 mm (more specifically, 2.4 mm). In order for this to be the portion for drawing out the tubular shaft 13, with a diameter of approximately 2 mm (more specifically, 2.1 mm), from inside the abdominal cavity, it has an inner diameter size substantially equal to the tubular shaft 13.

Figure 10:
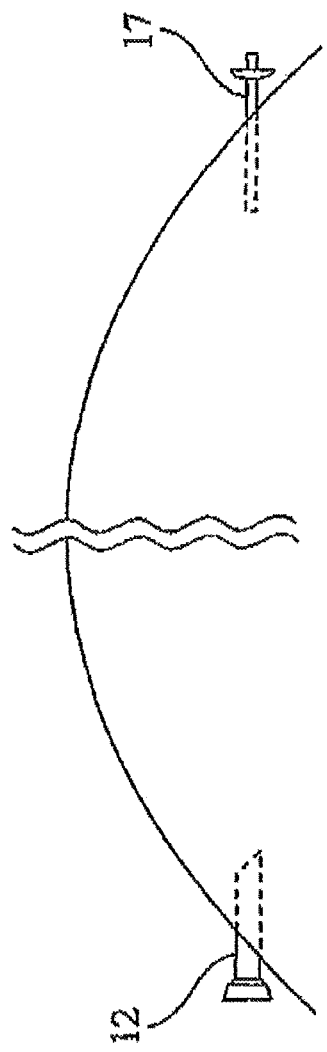
FIG. 10 schematically shows a usage state of a forceps unit according to the embodiment and is a schematic view of a state where a trocar and a small-diameter port are inserted in an abdominal region.

In using the forceps unit 11 for laparoscopic surgery, the trocar 12 with a diameter of substantially 5 mm that is to be the portion inserted inside the abdominal cavity is inserted into the abdominal region as shown in FIG. 10. Similarly, the small-diameter port 17 of small diameter that is to be the portion for drawing out the tubular shaft 13 from inside the abdominal cavity is inserted at a different position of the abdominal region across a fixed interval from the trocar 12.

Figure 11:
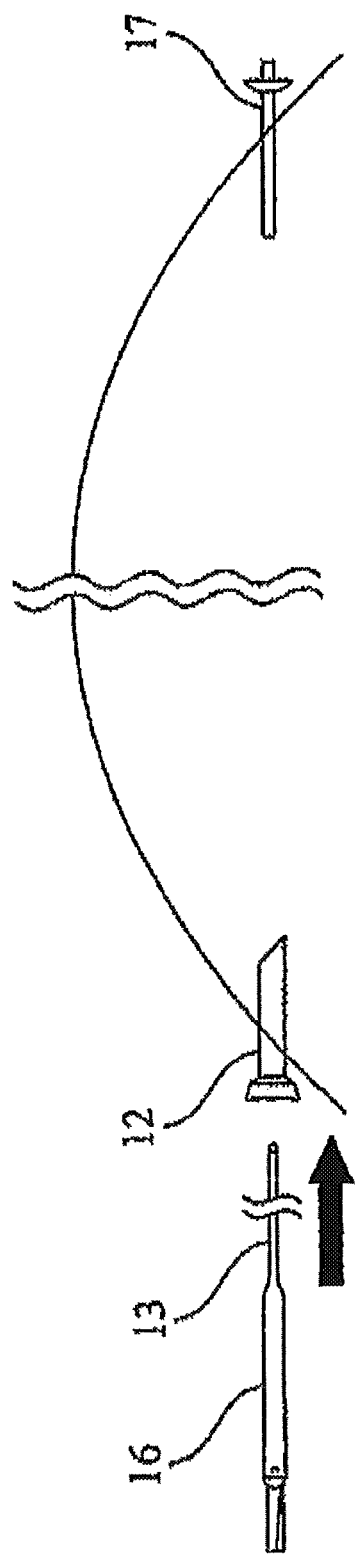
FIG. 11 is a schematic view of a state where small-diameter forceps are about to be inserted into the trocar.
Figure 12:
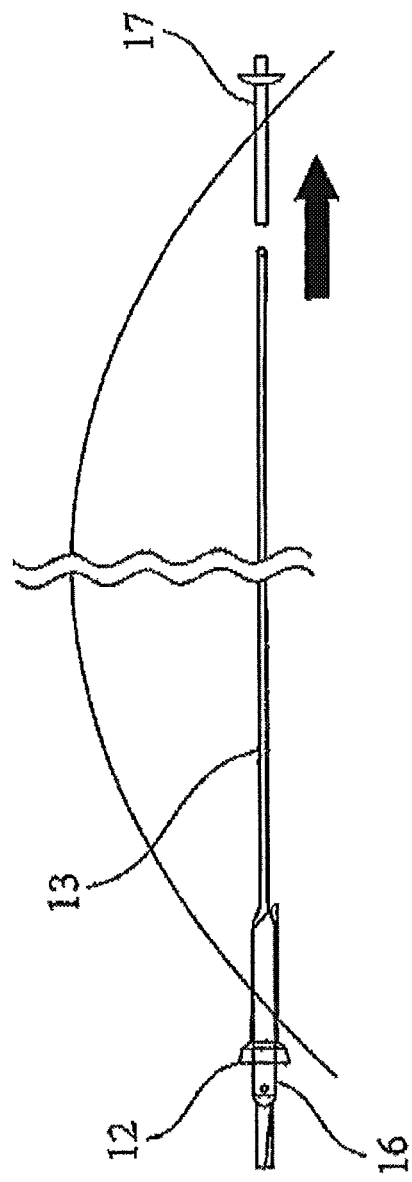
FIG. 12 is a schematic view of a state where the small-diameter forceps are inserted into the trocar.
Figure 13:
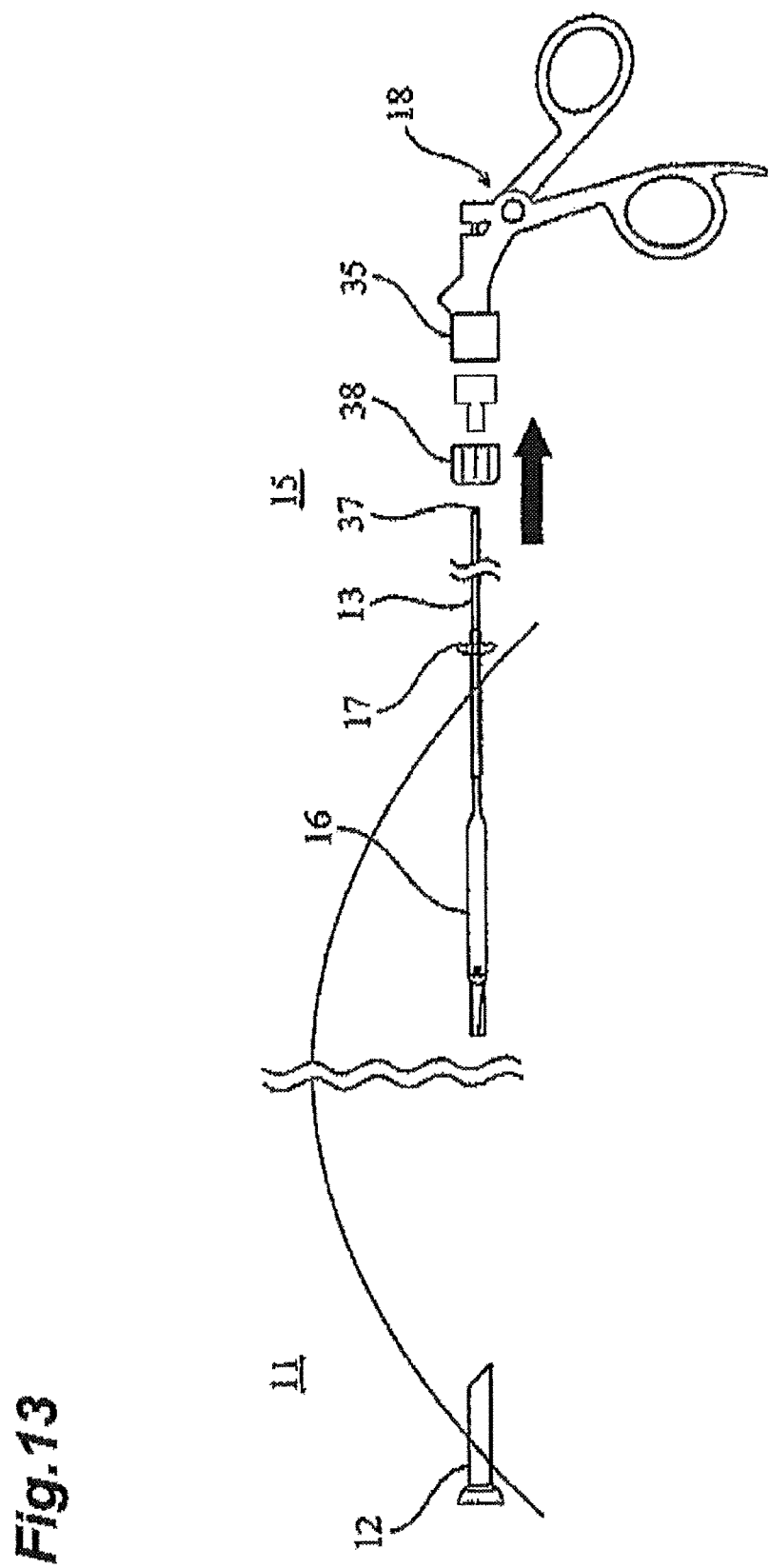
FIG. 13 is a schematic view of a state where a tubular shaft of the small-diameter forceps is drawn out from the small-diameter port.

In this state, the small-diameter forceps 15, with the handle 18 removed, is inserted, starting from the terminal end of the tubular shaft 13 of small diameter, into the abdominal cavity via the trocar 12 as shown in FIG. 11. Then, as shown in FIG. 12, the distal end of the tubular shaft 13 is directed toward the small-diameter port 17 and moved inside the abdominal cavity in the direction of the arrow. Thereafter, as shown in FIG. 13, the distal end of the tubular shaft 13 of the small-diameter forceps 15 is drawn out from the small-diameter port 17, and upon attaching the chuck member 40 and attaching the joint portion 37 of the inserted member 14 to the joint receptacle 36 of the handle 18, the fixing ring 38 is coupled to the coupling portion 35 at the front portion of the cylindrical main body 31a to mount the handle 18 onto the terminal end portion of the tubular shaft 13. In this state, the gripping portion 16 provided at the distal end of the tubular shaft 13 of the small-diameter forceps 15 is inside the abdominal cavity.

Figure 14:
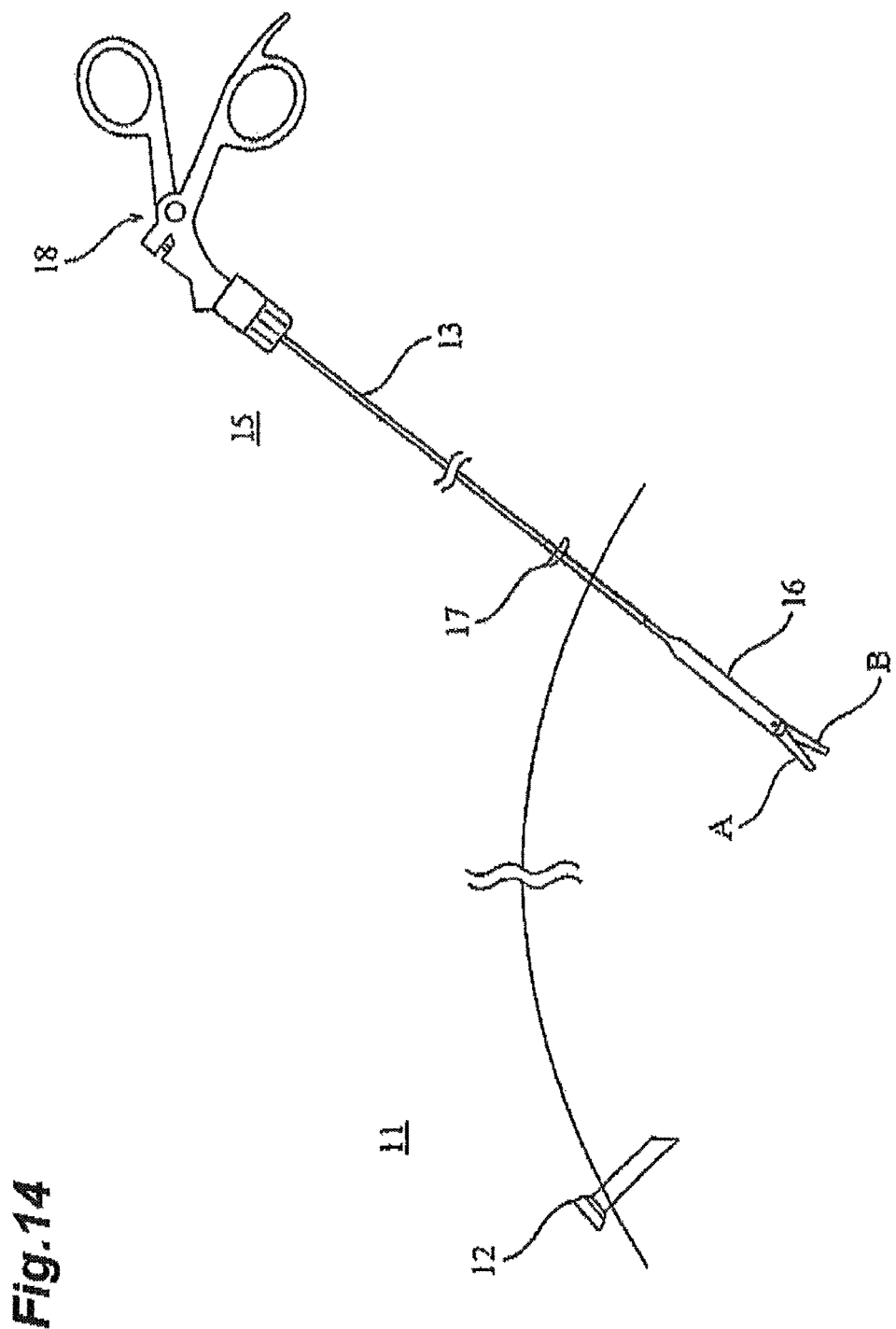
FIG. 14 is a schematic view schematically showing a usage state where a handle is mounted on an end portion of the tubular shaft of the small-diameter forceps to perform laparoscopic surgery.

By manipulating the handle 18 upon assembling as described above, the gripping portion 16 provided at the distal end of the tubular shaft 13 can be manipulated freely inside the abdominal cavity as shown in FIG. 14. FIG. 14 thus schematically shows a usage state where the handle 18 is mounted on the end portion of the tubular shaft 13 of the small-diameter forceps 15 and the small-diameter forceps 15 is used to perform endoscopic surgery in the abdominal cavity.

The forceps unit 11 may include a tubular shaft guide member 50 as an auxiliary tool for drawing out the end portion of the tubular shaft 13 from the small-diameter port 17. The shaft guide member 50 has a smaller diameter than the diameter of the insertion hole of the small-diameter port 17. For example, it has the same diameter as the terminal end 13c and the main body portion 13a of the tubular shaft 13. The shaft guide member 50 is connectable to the terminal end of the inserted member 14. For example, the inserted member 14 is inserted into the interior of the shaft guide member 50 and then fitted together.

Figure 15:
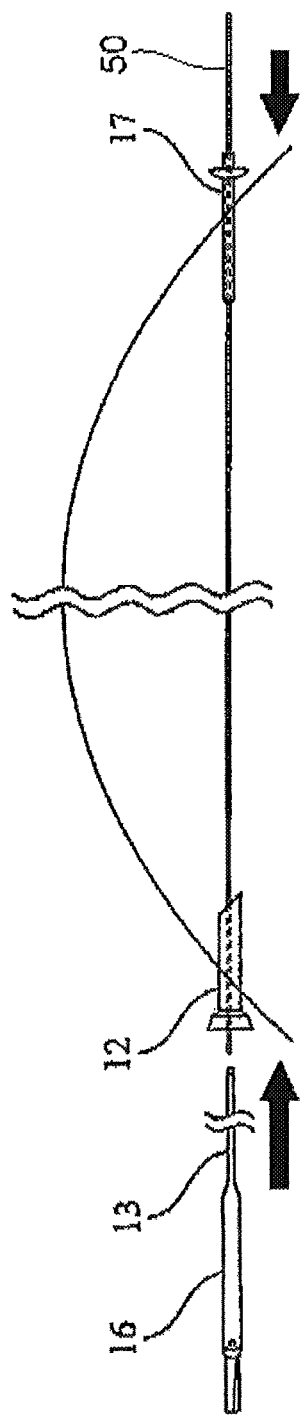
FIG. 15 is a schematic view of a state where the small-diameter forceps are about to be inserted into the trocar using a shaft guide.
Figure 16:
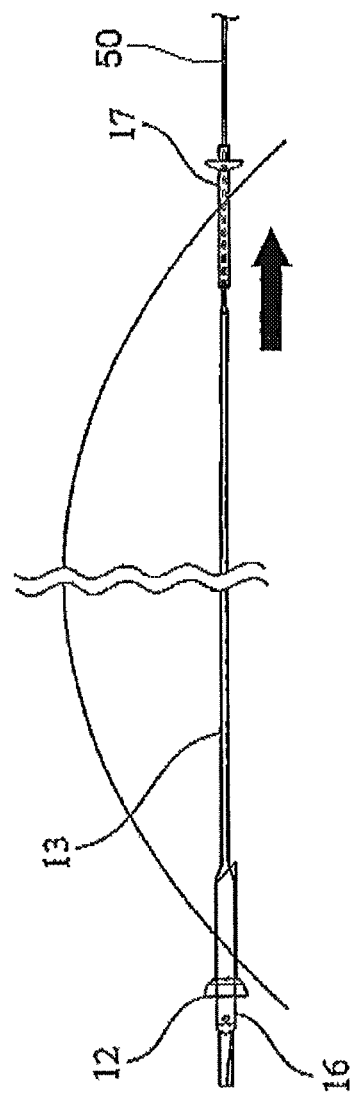
FIG. 16 is a schematic view of a state where the small-diameter forceps are inserted into the trocar using the shaft guide.
Figure 17:
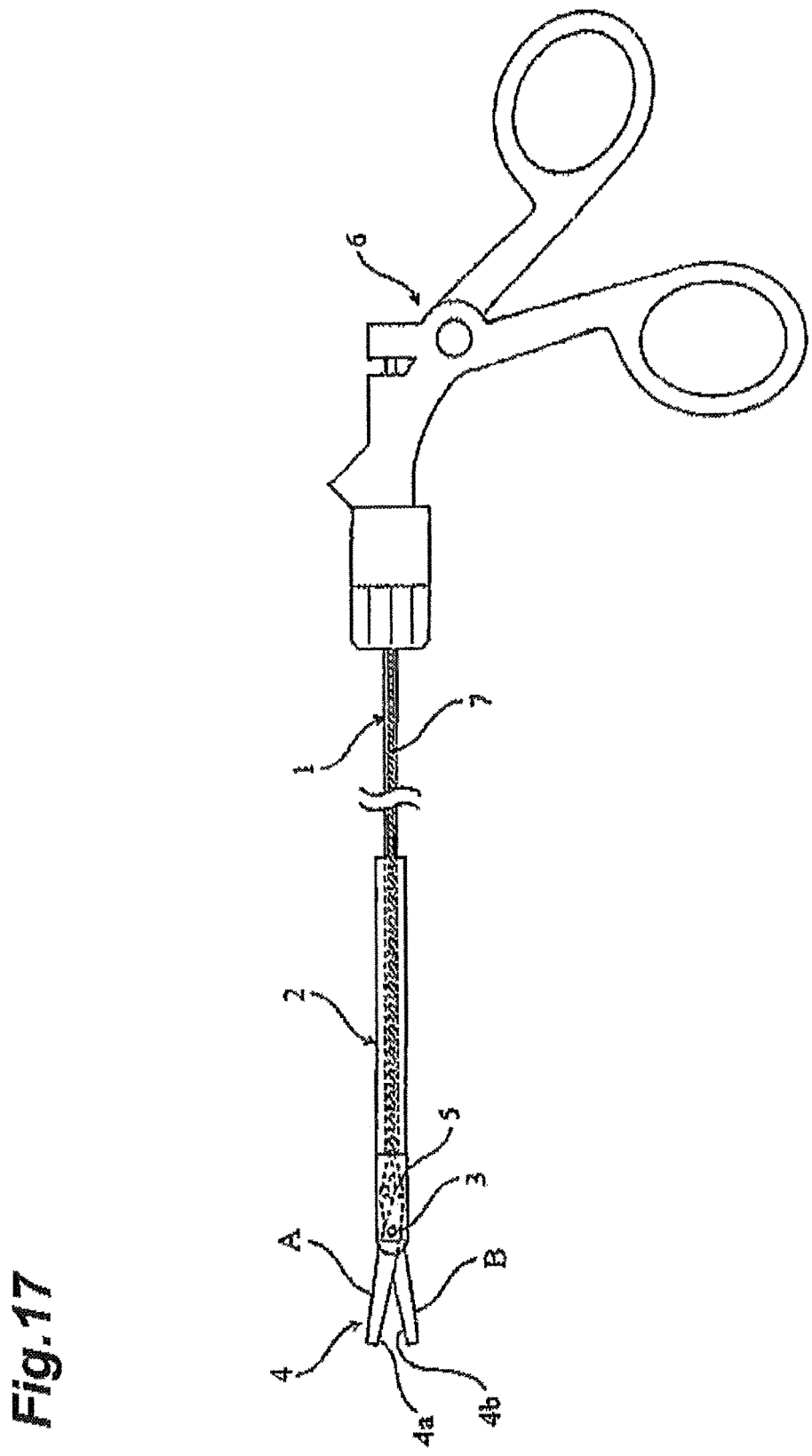
FIG. 17 is a side view of an example of conventional forceps.

An example of use of the shaft guide member 50 shall now be described. Here, it shall be assumed that a laparoscope is already inserted in the trocar 12. First, as shown in FIG. 15, one end portion of the shaft guide member 50 is inserted in the abdominal cavity via the small-diameter port 17. The shaft guide member 50 is then moved toward the laparoscope inserted in the trocar 12. The shaft guide member 50 is then inserted inside the trocar 12. One end portion of the shaft guide member 50 is then drawn outside the abdominal cavity via the trocar 12 and the one end portion of the shaft guide member 50 and the inserted member 14 are connected. At this point, the other end portion of the shaft guide member 50 is left outside the abdominal cavity via the small-diameter port 17. Thereafter, the inserted member 14 is pushed in and then drawn out from the trocar 12 as shown in FIG. 16. It is easier to insert a rod-like member from the small-diameter port 17 into the trocar 12 that is thicker than the small-diameter port 17 than to insert the rod-like member from the trocar 12 into the small-diameter port 17 that is thinner than trocar 12. By inserting the shaft guide member 50 beforehand, the axes of the trocar 12 and the small-diameter port 17 can be aligned. The insertion of the forceps 15 is thereby facilitated.

With the forceps 15 and the forceps unit 11 according to the embodiment described above, the diameter of the distal end 13b of the tubular shaft 13 is greater than the diameter of the main body 13a so that strength can be maintained in comparison to a case where the gripping portion 16 is attached to a tubular shaft 13 having a distal end 13b of the same diameter as a main body 13a. The size of the mounted gripping portion 16 can thereby be made large in accordance with the size of the distal end 13b of the tubular shaft 13. Gripping of various tissues can thus be accommodated. Also, by the handle 18 being detachable from the tubular shaft 13 and the joint portion 37 of the tubular shaft 13 being smaller in diameter than the diameter of the main body 13a of the tubular shaft 13, instead of inserting the forceps 15 into the abdominal cavity starting from the distal end 13b of the tubular shaft 13, the handle can be detached, the forceps (without the handle 18) can be inserted into the abdominal cavity starting from the terminal end 13c of the tubular shaft 13, and the terminal end 13c of the tubular shaft 13 can be drawn outside the abdominal cavity to attach the handle 18. That is, the size of a surgical wound for using the forceps 15 can be made approximately the same in size as a hole enabling insertion of the terminal end 13c and the main body 13a of the tubular shaft 13. Recently, from a cosmetic standpoint and a standpoint of quickness of recovery, it is becoming important to lessen the number of ports as much as possible in laparoscopic surgery. Further, it is being demanded that the ports be made as small as possible in size as well. However, due to being lower in the degree of freedom in comparison to a multiple incision surgery, a single incision surgery may require an auxiliary forceps. Also, depending on the object tissue to be gripped, it is necessary to make the gripping portion large and consequently the size of the port for the auxiliary forceps cannot be made small. With the forceps 15 and the forceps unit 11 according to the embodiment, the size of the surgical wound can be made small regardless of the size of the distal end of the forceps 15 or the size of the gripping portion 16. The forceps are thus especially useful as auxiliary forceps.

Also, with the forceps 15 and the forceps unit 11 according to the embodiment, the handle 18 and the tubular shaft 13 can be fixed detachably using the chuck member 40 and the fixing ring 38. A detachable coupling structure can thus be realized without enlarging the sizes of the diameters of the inserted member 14 and the tubular shaft 13 that influence the size of the surgical wound.

Further with the forceps unit 11 according to the embodiment, by the shaft guide member 50 being included, it is possible, before inserting the forceps 15, with the handle 14 removed, into the trocar 12, to insert the one end portion of the shaft guide member 50 into the small-diameter port 17 and to draw out the one end portion of the shaft guide member 50 via the trocar 12 and connect it to the terminal end of the inserted member 14 without the other end portion of the shaft guide member 50 being inserted into the abdominal cavity. By then extracting the other end portion of the shaft guide member 50 from the small-diameter port 17, the terminal end 13c of the tubular shaft 13 can be drawn out easily to the exterior of the abdominal cavity.

Although with the embodiment, various descriptions were provided for the case where the size of the tubular shaft 13 is approximately 2 mm, the present invention is not restricted in particular in size.

Also, as usages of the forceps 15 and the forceps unit 11 for laparoscopic surgery of the embodiment, applications to forceps used suitably in such usages as hemostasis or tissue gripping of a tissue of a target site inside an abdominal cavity, gripping of a suture, or removal of a foreign object, etc., are also possible.

REFERENCE SIGNS LIST

11 . . . forceps unit, 12 . . . trocar, 13 . . . tubular shaft, 14 . . . inserted member, 15 . . . small-diameter forceps, 16 . . . gripping portion, A, B . . . gripping members, 17 . . . small-diameter port, 18 . . . handle, 21 . . . rotation shaft, 22 . . . distal end portion, 22a, 22b . . . object-facing surfaces, 23 . . . pulling portion, 31 . . . fixed member, 31a . . . cylindrical main body, 32 . . . rotation shaft, 33 . . . movable member, 34 . . . pulling lever, 35 . . . coupling portion (fixing portion) 36 . . . joint receptacle (fixing portion), 38 . . . fixing ring (fixing portion).

The invention claimed is:

1. A forceps for gripping tissue, the forceps comprising:
a rod-like tubular shaft having a penetrating hole formed in an axial direction;
a rod-like inserted member inserted inside the tubular shaft and being movable in the axial direction inside the tubular shaft;
a gripping portion provided at a distal end of the inserted member and coupled to a distal end of the tubular shaft, the gripping portion including a pair of gripping members capable of opening and closing, each of the gripping members having a distal end portion that applies a force for gripping on the tissue and a pulling portion to which the force for gripping is applied via movement of the inserted member;
a handle coupled to a terminal end of the inserted member; and
a fixing portion detachably fixing the handle to the tubular shaft in a state where the handle is coupled to the inserted member; and
wherein a main body of the tubular shaft includes a mid-section of the tubular shaft between a terminal end of the tubular shaft and the distal end of the tubular shaft,
wherein the distal end of the tubular shaft has a larger diameter than a diameter of the terminal end of the tubular shaft and a diameter of an entirety of the main body of the tubular shaft,
wherein the distal end of the tubular shaft is coupled to a connecting portion at a terminal end of the gripping portion,
wherein a joint portion, having a smaller diameter than the diameter of the entirety of the main body of the tubular shaft, is formed at the terminal end of the inserted member, and the handle is provided with a joint receptacle that houses the joint portion and is advanced and retracted by manipulation of the handle,
wherein the fixing portion includes:
a chuck member having an insertion hole formed therein and configured for locking the terminal end of the tubular shaft in the axial direction, and
a fixing ring having an insertion hole formed therein and coupled to a coupling portion provided on the handle, and
wherein the chuck member is fixed by the fixing ring to the handle in a state in which the terminal end of the tubular shaft, with the inserted member inserted therein, is inserted in the chuck member and the fixing ring, the joint receptacle of the handle and the joint portion of the inserted member are coupled, and the chuck member is sandwiched between the fixing ring and the handle,
wherein the chuck member and the fixing ring are separable from the handle, and the distal end of the tubular shaft into which the inserted member is inserted is inserted into the chuck member and the fixing ring separated from the handle, and
wherein the fixing ring is not fixed to the tubular shaft when the fixing ring is separated from the handle.

2. The forceps according to claim 1, wherein the tubular shaft is formed so that a size of its diameter changes gradually.

3. The forceps according to claim 1, wherein a diameter of the terminal end of the gripping portion is equal to the diameter of the distal end of the tubular shaft.

4. The forceps according to claim 1, wherein the tubular shaft is formed with a single member.

5. The forceps according to claim 1, wherein the chuck member has a projecting step portion for locking the terminal end of the tubular shaft in the axial direction, wherein the projecting step portion is provided along an inner circumference of the insertion hole, and wherein the chuck member is fixed by the fixing ring to the handle in a state in which the terminal end of the tubular shaft is abutted against the projecting step portion of the chuck member.

6. The forceps according to claim 1, wherein the joint receptacle of the handle is contained in the chuck member.

7. The forceps according to claim 1, wherein the chuck member has a circular cylindrical main body portion and a tubular guide portion.

8. The forceps according to claim 7, wherein the tubular guide portion has slits formed along the axial direction in the tubular guide portion.

9. The forceps according to claim 1, wherein the diameter of the terminal end of the tubular shaft is the same as the diameter of the entirety of the main body.

10. A forceps unit, comprising:
a trocar serving as a portion for insertion into an abdominal cavity;
forceps for gripping tissue and including:
a tubular shaft,
a rod-like inserted member inserted inside the tubular shaft and being movable in an axial direction inside the tubular shaft,
a gripping portion provided at a distal end of the inserted member and coupled to a distal end of the tubular shaft, the gripping portion including a pair of gripping members capable of opening and closing, each of the gripping members having a distal end portion that applies a force for gripping on the tissue and a pulling portion to which the force for gripping is applied via movement of the inserted member,
a handle coupled to a terminal end of the inserted member, and
a fixing portion detachably fixing the handle to the tubular shaft in a state where the handle is coupled to the inserted member; and
a small-diameter port of small diameter insertable in the abdominal cavity and serving as a portion for drawing out the tubular shaft from inside the abdominal cavity; and
wherein a main body of the tubular shaft includes a mid-section of the tubular shaft between a terminal end of the tubular shaft and the distal end of the tubular shaft,
wherein the distal end of the tubular shaft has a larger diameter than a diameter of an entirety of the main body of the tubular shaft and a diameter of an insertion hole of the small-diameter port,
wherein the distal end of the tubular shaft is coupled to a connecting portion at a terminal end of the gripping portion,
wherein the main body and the terminal end of the tubular shaft have diameters smaller than the diameter of the insertion hole of the small-diameter port, and
wherein a joint portion, having a smaller diameter than the diameters of the entirety of the main body and the terminal end of the tubular shaft, is formed at the terminal end of the inserted member, and the handle is provided with a joint receptacle that houses the joint portion and is advanced and retracted by manipulation of the handle,
wherein the fixing portion includes:
a chuck member having an insertion hole formed therein and configured for locking the terminal end of the tubular shaft in the axial direction, and
a fixing ring having an insertion hole formed therein and coupled to a coupling portion provided on the handle, and wherein the chuck member is fixed by the fixing ring to the handle in a state in which the terminal end of the tubular shaft, with the inserted member inserted therein, is inserted in the chuck member and the fixing ring, the joint receptacle of the handle and the joint portion of the inserted member are coupled, and the chuck member is sandwiched between the fixing ring and the handle, wherein the chuck member and the fixing ring are separable from the handle, and the distal end of the tubular shaft into which the inserted member is inserted is inserted into the chuck member and the fixing ring separated from the handle, and wherein the fixing ring is not fixed to the tubular shaft when the fixing ring is separated from the handle.

11. The forceps unit according to claim 10, further comprising a tubular shaft guide member connectable to the terminal end of the inserted member and having a smaller diameter than the diameter of the insertion hole of the small-diameter port, wherein the tubular shaft guide member is insertable in the trocar and the small-diameter port.

* * * * *